United States Patent
Tsukaguchi

[11] Patent Number: 5,769,932
[45] Date of Patent: Jun. 23, 1998

[54] SURFACE TREATMENT MATERIAL REQUIRED IN FUSING DENTAL PORCELAIN WHICH PREVENTS DEPOSITION OF COAT DUE TO ANTIOXIDANT AND STRONGLY BONDS METAL FRAME AND DENTAL PORCELAIN WITH EACH OTHER

[75] Inventor: Mamoru Tsukaguchi, Osaka, Japan

[73] Assignee: Yamamoto Kikinzoku Jigane Co., Ltd., Osaka, Japan

[21] Appl. No.: 747,025

[22] Filed: Nov. 7, 1996

[30] Foreign Application Priority Data

Nov. 13, 1995 [JP] Japan .................................. 7-294531

[51] Int. Cl.⁶ ...................................................... B22F 7/00
[52] U.S. Cl. ..................... 106/35; 106/1.13; 106/1.18; 106/1.23; 106/1.26
[58] Field of Search ........................... 106/35, 1.13, 1.18, 106/1.23, 1.26

[56] References Cited

U.S. PATENT DOCUMENTS

| | | | |
|---|---|---|---|
| 4,010,048 | 3/1977 | Tesk et al. | 148/24 |
| 4,426,404 | 1/1984 | Shoher et al. | 427/2 |
| 4,468,251 | 8/1984 | Hausselt et al. | 106/1.18 |
| 4,992,098 | 2/1991 | Lotze et al. | 106/1.23 |
| 5,059,242 | 10/1991 | Firmstone et al. | 106/1.36 |

FOREIGN PATENT DOCUMENTS

| | | |
|---|---|---|
| 3828430 A1 | 3/1990 | Germany . |
| 5-177380 | 7/1993 | Japan . |
| 5-177381 | 7/1993 | Japan . |
| 5-254949 | 10/1993 | Japan . |

OTHER PUBLICATIONS

"Patent Abstracts of Japan", to vol. 96, No. 001 (JP 08–003013A), Jan. 9, 1996.

*Primary Examiner*—Melissa Bonner
*Attorney, Agent, or Firm*—Rabin, Champagne, & Lynt, P.C.

[57] ABSTRACT

A surface treatment material used in fusing dental porcelain, containing powder of gold terpene sulfide, is applied and sintered on a metal frame. Then, the terpene and sulfur oxidize to suppress oxidation of gold and the like. A surface treatment layer having no coat, is thus formed on the surface of the metal frame with the alloy component of the metal frame and gold being bonded and combined with each other in a diffusion and solid solution manner. Then, it is fused with a dental porcelain built up on the surface of the metal frame on which the surface treatment layer is formed.

13 Claims, 3 Drawing Sheets

PRIOR ART

५,७६९,९३२

SURFACE TREATMENT MATERIAL REQUIRED IN FUSING DENTAL PORCELAIN WHICH PREVENTS DEPOSITION OF COAT DUE TO ANTIOXIDANT AND STRONGLY BONDS METAL FRAME AND DENTAL PORCELAIN WITH EACH OTHER

BACKGROUND OF THE INVENTION

1. Field of the Invention

The present invention relates to a surface treatment material required in fusing dental porcelain, and particularly to a surface treatment material used when fusing dental porcelain for artificial, teeth on a metal frame.

2. Description of the Background Art

A surface treatment material required in fusing dental porcelain has been proposed in Japanese Patent Application No. 6-135794.

This surface treatment material contains powder of a binary eutectic alloy of gold and silicon and antioxidant, such as rosin or sodium borate, kneaded into paste with a binder, such as monoethanolamine or diethanolamine.

When the surface treatment material 2 required in fusing dental porcelain is applied to a metal frame 1 as shown in FIG. 4(1) and sintered, then gold in the treatment material an alloy component in the metal frame 1 mutually penetrate into texture of each other and bonded in a diffusion and solid solution manner, which forms a surface treatment layer 20 on the surface of the metal frame 1 as shown in FIG. 4(2). When the surface treatment material 2 is sintered, the antioxidant contained therein is deposited on the surface of the surface treatment layer 20 as a coat 21. Since the coat 21 causes cracking of a dental porcelain fused later, the coat 21 is removed by cleaning with dilute hydrochloric acid or the like. A dental porcelain 3 is fused on the surface treatment layer 20 after the coat 21 is removed, and then silicon in the surface treatment layer 20 formed on the surface of the metal frame and silicon of the dental porcelain component are mutually bonded in a diffusion and solid solution manner.

Thus the metal frame 1 is coated with the dental porcelain 3 as shown in FIG. 4(3), thereby producing an artificial tooth.

However, the surface treatment material required in fusing dental porcelain requires the process of cleaning with a dilute hydrochloric acid or the like to remove the coat 21 of the antioxidant formed on its surface after it is sintered on the metal frame 1, presenting inconvenience in use.

SUMMARY OF THE INVENTION

In a surface treatment material for a metal frame required to fuse a dental porcelain on the metal frame, an object of the present invention is to eliminate the need for the step of cleaning a surface treatment layer 20 after the surface treatment material is sintered so as to simplify the process of manufacturing an artificial tooth and so as to improve the finished condition.

In order to achieve the object above, in a first aspect of the present invention to a surface treatment material; required in fusing dental porcelain is a paste containing a powder of gold terpene sulfide as an effective component.

When the surface treatment material required in fusing dental porcelain is applied and sintered on a metal frame terpene and sulfur contained in the gold terpene sulfide, which are more oxidizable than gold and other contained components, oxidize earlier and suppress oxidation of gold and the like. As sulfur providing the function of suppressing oxidation (referred to as "oxidation suppressing function" hereinafter) volatilizes as $SO_2$ when sintered, and terpene $(C_5H_8)_n$ is decomposed into $CO_2$ and $H_2O$ and released into the air, a surface treatment layer having no coat, (i.e., such as found on a conventional one) is formed on the surface of the metal frame 1, and the alloy component of the metal frame and gold are bonded and combined with each other in a diffusion and solid solution manner. Then it is fused with a dental porcelain put on the surface of the metal frame having the surface treatment layer.

The gold component in the surface treatment layer reacts with the dental porcelain layer after fused to form light yellow or orange color.

In order to achieve the object above, according to a second aspect of the present invention, the surface treatment material required in fusing dental porcelain of the first aspect further contains a powder of silicon terpene sulfide and/or a powder of aluminum terpene sulfide.

In the case of the above-mentioned surface treatment material required in fusing dental porcelain, terpene and sulfur in the effective components exhibit the oxidation suppressing function when sintered by the same function as that of the first aspect to prevent oxidation of gold, silicon and aluminum. After sintered, when it is sintered on a metal frame, alloy component of the metal frame and gold are mutually bonded and combined in a diffusion and solid solution manner. Since the surface treatment layer contains silicon or aluminum, when it is fused with a dental porcelain put on the surface of the surface treatment layer, silicon or aluminum in the ceramic component and silicon or aluminum in the surface treatment layer are bonded with each other in a diffusion and solid solution manner.

In order to achieve the object above, according to a third aspect of the present invention, the surface treatment material required in fusing dental porcelain according to first and second aspects further contains one or more kinds of powders out of a powder of tin terpene sulfide, a powder of indium terpene sulfide and a powder of iron terpene sulfide.

While it is generally known that "tin" of tin terpene sulfide, "indium" of indium terpene sulfide, and "iron" of iron terpene sulfide improve wettability between the surface treatment layer and the dental porcelain, those containing the effective components above further improve the fit between the dental porcelain and the surface treatment layer.

In order to achieve the object above, according to a surface treatment material of a fourth aspect of the present invention, the surface treatment material required in fusing dental porcelain according to any of first through third aspects further contains a powder of silver terpene sulfide, or a powder of silver.

As is well known, since silver has a lower melting point than gold and good atom diffusion property, silver melts earlier than gold in the sintering process to diffuse and form a solid solution in the texture of the metal frame. Accordingly, excessive diffusion of gold into the metal frame is suppressed by setting the sintering temperature for the surface treatment material required in fusing dental porcelain lower than the melting point of gold (e.g., 900°–1000° C.) and setting the sintering time short (e.g., about one minute). This prevents the gold color of the surface treatment layer from becoming lighter, which ensures the gold color even if the coating layer is thin.

Terpene and sulfur contained in gold terpene sulfide and the like exhibit the oxidation suppressing function as explained in the first aspect and the oxidation suppressing function also effectively works on the silver component.

In order to achieve the object above, according to a surface treatment material of a fifth aspect of the present invention, the surface treatment material required in fusing dental porcelain according to any of first through fourth aspects further contains one or more kinds of powders out of a powder of a binary eutectic alloy of gold and silicon, a powder of a binary eutectic alloy of gold and aluminum, a powder of a binary eutectic alloy of gold and tin, a powder of a binary eutectic alloy of gold and indium.

While each powder of the binary eutectic alloys has the function of improving the bonding strength of the dental porcelain and the metal frame as shown in Japanese Patent Application No. 6-135794, the oxidation suppressing function by terpene and sulfur in the above effective components effectively works also on these binary eutectic alloys.

In order to achieve the object above, according to a surface treatment material in a sixth aspect of the present invention, the surface treatment material required in fusing dental porcelain according to any of the first through fifth aspects further contains an alloyed powder of two or more kinds selected out of silicon, aluminum, tin, and indium with gold.

It is possible to use each of the powders above as a surface treatment material required in fusing dental porcelain by adding an antioxidant. If a dental porcelain is fused with those added to the surface treatment material required in fusing dental porcelain of the first through fourth aspects, however, terpene and sulfur contained in gold terpene sulfide or the like exhibit the oxidation suppressing function as explained in the first aspect, which also prevents oxidation of the alloy.

As has been described above, according to the first through to sixth aspects of the present invention, it does not need the special process of cleaning the surface treatment layer formed on the surface of the metal frame when the surface treatment material required in fusing dental porcelain is sintered because a coat is not formed on the surface of the surface treatment layer, which improves the efficiency of production of an artificial tooth.

Furthermore, since the cleaning process is not needed, inferior finish due to inferior cleaning or the like is prevented.

Moreover, it is possible to cause the thin region of the dental porcelain layer extending from teeth to gums to appear light yellow or orange, so that change in color tone in the region shifting from teeth to gums in the dental porcelain layer covering the metal frame (expression of continuous transition in color tone from teeth to gums) can be made continuous, and then it will be extremely close to healthy teeth.

According to the third aspect of the present invention, since the wettability of the surface treatment layer and the dental porcelain built up thereon can be improved to improve a fit between the two, the dental porcelain can be firmly fused on the surface treatment layer.

According to the fourth aspect of the present invention, since the color of the coat of the surface treatment layer formed on the metal frame can be still closer to gold, the color of the thin porcelain layer shifting from teeth to gums can be made closer to yellow or orange. This produces the effect of finishing that region to a color still closer to that of healthy teeth.

According to the fifth aspect of the present invention, since terpene and sulfur contained in gold terpene sulfide and the like prevent oxidation of each binary eutectic alloy, the binary eutectic alloys can be used without the need of adding a special antioxidant.

According to the sixth aspect of the present invention terpene and sulfur contained in gold terpene sulfide and the like prevent oxidation of each added alloy, so that the alloy can be used without a special antioxidant.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
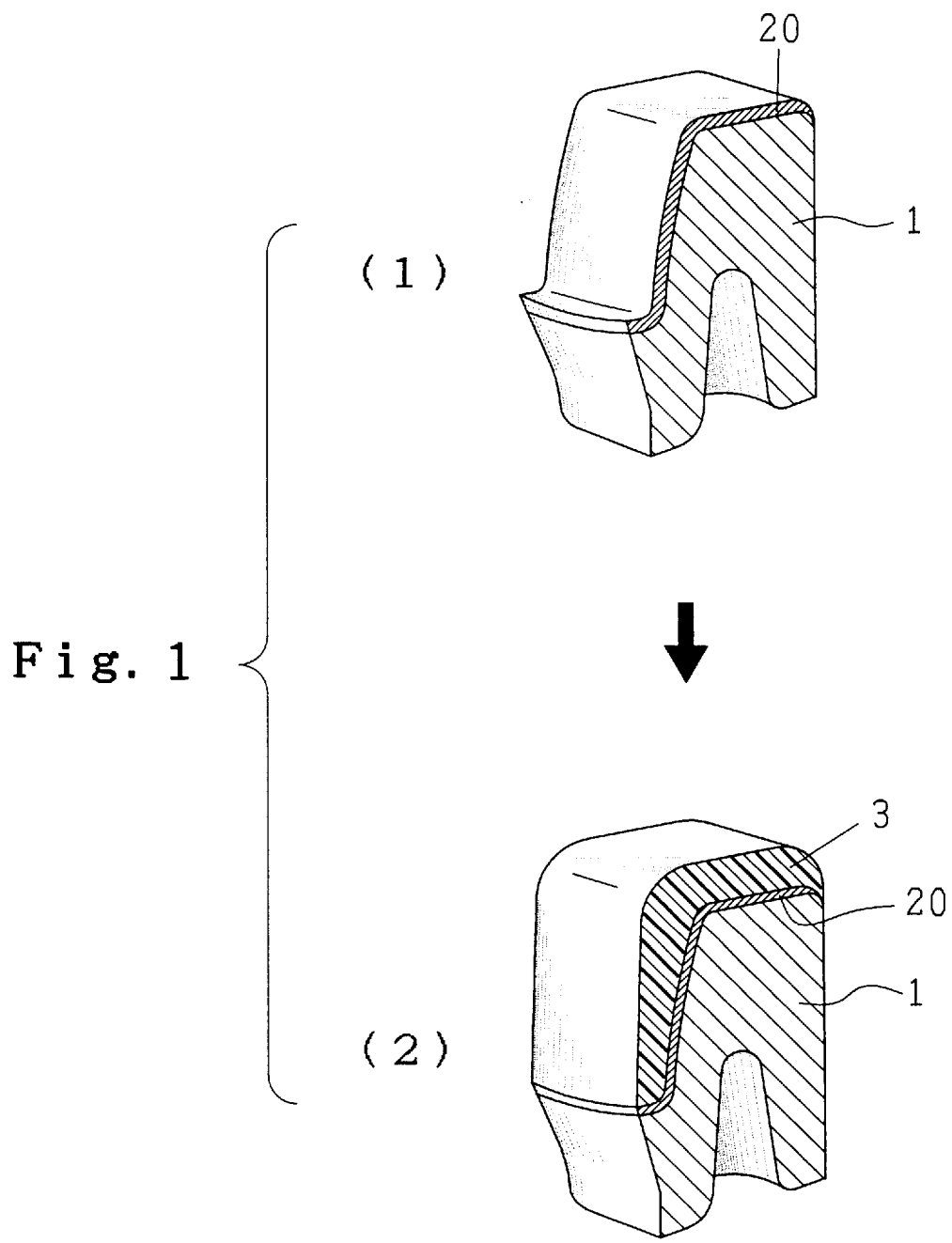
FIG. 1 is a diagram showing process of fusing a dental porcelain on a metal frame using a surface treatment material required in fusing dental porcelain according to an embodiment of the present invention.

In any of the embodiments shown below, glycerol is used as a binder to obtain a paste-like surface treatment material 2 required in fusing dental porcelain. As the binder, as well as glycerol, terpineol, ethylene glycol, diethylene glycol, polypropylene glycol, diethanolamine, and triethanolamine can be used.

TABLE 1

| Sample No. | Kind of terpene sulfide compound and mixture ratio (wt %) | | | | | | | | |
|---|---|---|---|---|---|---|---|---|---|
| | Au—S—R | Si—S—R | Al—S—R | Sn—S—R | In—S—R | Fe—S—R | Ga—S—R | Ge—S—R | Ag—S—R |
| 1 | 87~99 | 1~13 | — | — | — | — | — | — | — |
| 2 | 87~99 | — | 1~13 | — | — | — | — | — | — |
| 3 | 87~99 | 0.5~6.5 | 0.5~6.5 | — | — | — | — | — | — |
| 4 | 86~98 | 1~13 | — | 0.1~1 | — | — | — | — | — |
| 5 | 86~98 | 1~13 | — | — | 0.1~1 | — | — | — | — |
| 6 | 86~98 | 1~13 | — | — | — | 0.1~1 | — | — | — |
| 7 | 86~98 | 1~13 | — | — | — | — | 0.1~1 | — | — |
| 8 | 86~98 | 1~13 | — | — | — | — | — | 0.1~1 | — |

TABLE 1-continued

| | | | | | | | | | |
|---|---|---|---|---|---|---|---|---|---|
| 9 | 86~98 | — | 1~13 | 0.1~1 | — | — | — | — | — |
| 10 | 86~98 | — | 1~13 | — | 0.1~1 | — | — | — | — |
| 11 | 86~98 | — | 1~13 | — | — | 0.1~1 | — | — | — |
| 12 | 86~98 | — | 1~13 | — | — | — | 0.1~1 | — | — |
| 13 | 86~98 | — | 1~13 | — | — | — | — | 0.1~1 | — |
| 14 | 80~99 | 0.25~10 | 0.25~9.5 | 0.1~0.5 | — | — | — | — | — |
| 15 | 80~99 | 0.25~10 | 0.25~9.5 | — | 0.1~0.5 | — | — | — | — |
| 16 | 80~99 | 0.25~10 | 0.25~9.5 | — | — | 0.1~0.5 | — | — | — |
| 17 | 80~99 | 0.25~10 | 0.25~9.5 | — | — | — | 0.1~0.5 | — | — |
| 18 | 80~99 | 0.25~10 | 0.25~9.5 | — | — | — | — | 0.1~0.5 | — |
| 19 | 80~98 | 0.25~10 | 0.25~9.5 | 0.1~0.5 | 0.1~0.5 | — | — | — | — |
| 20 | 80~96 | 0.25~10 | 0.25~9.5 | 0.1~0.5 | 0.1~0.5 | 0.1~0.5 | 0.1~0.5 | 0.1~.05 | — |
| 21 | 80~98 | 1~10 | — | — | — | — | — | — | 0.5~10 |
| 22 | 80~98 | — | 1~10 | — | — | — | — | — | 0.5~10 |
| 23 | 80~98 | 1~10 | — | — | — | — | — | — | — |
| 24 | 80~98 | — | 1~10 | — | — | — | — | — | — |
| 25 | 80~98 | 0.5~10 | — | 0.1~0.5 | — | — | — | — | 0.5~10 |

| Sample No. | Ag fine powder | Kind of eutectic alloy and mixture ratio (wt %) | | | |
|---|---|---|---|---|---|
| | | AuSi | AuAl | AuSn | AuIn |
| 1 | — | — | — | — | — |
| 2 | — | — | — | — | — |
| 3 | — | — | — | — | — |
| 4 | — | — | — | — | — |
| 5 | — | — | — | — | — |
| 6 | — | — | — | — | — |
| 7 | — | — | — | — | — |
| 8 | — | — | — | — | — |
| 9 | — | — | — | — | — |
| 10 | — | — | — | — | — |
| 11 | — | — | — | — | — |
| 12 | — | — | — | — | — |
| 13 | — | — | — | — | — |
| 14 | — | — | — | — | — |
| 15 | — | — | — | — | — |
| 16 | — | — | — | — | — |
| 17 | — | — | — | — | — |
| 18 | — | — | — | — | — |
| 19 | — | — | — | — | — |
| 20 | — | — | — | — | — |
| 21 | — | — | — | — | — |
| 22 | — | — | — | — | — |
| 23 | 0.5~10 | — | — | — | — |
| 24 | 0.5~10 | — | — | — | — |
| 25 | — | — | — | — | — |

TABLE 2

| Sample No. | Kind of terpene sulfide compound and mixture ratio (wt %) | | | | | | | | |
|---|---|---|---|---|---|---|---|---|---|
| | Au—S—R | Si—S—R | Al—S—R | Sn—S—R | In—S—R | Fe—S—R | Ga—S—R | Ge—S—R | Ag—S—R |
| 26 | 80~98 | 0.5~10 | — | — | 0.1~0.5 | — | — | — | 0.5~10 |
| 27 | 80~98 | 0.5~10 | — | — | — | 0.1~0.5 | — | — | 0.5~10 |
| 28 | 80~98 | 0.5~10 | — | — | — | — | 0.1~0.5 | — | 0.5~10 |
| 29 | 80~98 | 0.5~10 | — | — | — | — | — | 0.1~0.5 | 0.5~10 |
| 30 | 80~98 | 0.5~10 | — | 0.1~0.5 | 0.1~0.5 | — | — | — | 0.5~10 |
| 31 | 80~98 | 0.5~10 | — | 0.1~0.5 | 0.1~0.5 | 0.1~0.5 | 0.1~0.5 | 0.1~0.5 | 0.5~10 |
| 32 | 80~98 | 0.5~10 | — | 0.1~0.5 | — | — | — | — | — |
| 33 | 80~98 | 0.5~10 | — | — | 0.1~0.5 | — | — | — | — |
| 34 | 80~98 | 0.5~10 | — | — | — | 0.1~0.5 | — | — | — |
| 35 | 80~98 | 0.5~10 | — | — | — | — | 0.1~0.5 | — | — |
| 36 | 80~98 | 0.5~10 | — | — | — | — | — | 0.1~0.5 | — |
| 37 | 80~98 | 0.5~10 | — | 0.1~0.5 | 0.1~0.5 | — | — | — | — |
| 38 | 80~98 | 0.5~10 | — | 0.1~0.5 | 0.1~0.5 | 0.1~0.5 | 0.1~0.5 | 0.1~0.5 | — |
| 39 | 80~98 | — | 0.5~10 | 0.1~0.5 | — | — | — | — | 0.5~10 |
| 40 | 80~98 | — | 0.5~10 | — | 0.1~0.5 | — | — | — | 0.5~10 |
| 41 | 80~98 | — | 0.5~10 | — | — | 0.1~0.5 | — | — | 0.5~10 |
| 42 | 80~98 | — | 0.5~10 | — | — | — | 0.1~0.5 | — | 0.5~10 |
| 43 | 80~98 | — | 0.5~10 | — | — | — | — | 0.1~0.5 | 0.5~10 |
| 44 | 80~98 | — | 0.5~10 | 0.1~0.5 | 0.1~0.5 | — | — | — | 0.5~10 |
| 45 | 80~98 | — | 0.5~10 | 0.1~0.5 | 0.1~0.5 | 0.1~0.5 | 0.1~0.5 | 0.1~0.5 | 0.5~10 |
| 46 | 80~98 | — | 0.5~10 | 0.1~0.5 | — | — | — | — | — |
| 47 | 80~98 | — | 0.5~10 | — | 0.1~0.5 | — | — | — | — |

TABLE 2-continued

| | | | | | | | | |
|---|---|---|---|---|---|---|---|---|
| 48 | 80~98 | — | 0.5~10 | — | — | 0.1~0.5 | — | — | — |
| 49 | 80~98 | — | 0.5~10 | — | — | — | 0.1~0.5 | — | — |
| 50 | 80~98 | — | 0.5~10 | — | — | — | — | 0.1~0.5 | — |

| Sample No. | Ag fine powder | Kind of eutectic alloy and mixture ratio (wt %) | | | |
|---|---|---|---|---|---|
| | | AuSi | AuAl | AuSn | AuIn |
| 26 | — | — | — | — | — |
| 27 | — | — | — | — | — |
| 28 | — | — | — | — | — |
| 29 | — | — | — | — | — |
| 30 | — | — | — | — | — |
| 31 | — | — | — | — | — |
| 32 | 0.5~10 | — | — | — | — |
| 33 | 0.5~10 | — | — | — | — |
| 34 | 0.5~10 | — | — | — | — |
| 35 | 0.5~10 | — | — | — | — |
| 36 | 0.5~10 | — | — | — | — |
| 37 | 0.5~10 | — | — | — | — |
| 38 | 0.5~10 | — | — | — | — |
| 39 | — | — | — | — | — |
| 40 | — | — | — | — | — |
| 41 | — | — | — | — | — |
| 42 | — | — | — | — | — |
| 43 | — | — | — | — | — |
| 44 | — | — | — | — | — |
| 45 | — | — | — | — | — |
| 46 | 0.5~10 | — | — | — | — |
| 47 | 0.5~10 | — | — | — | — |
| 48 | 0.5~10 | — | — | — | — |
| 49 | 0.5~10 | — | — | — | — |
| 50 | 0.5~10 | — | — | — | — |

TABLE 3

| Sample No. | Kind of terpene sulfide compound and mixture ratio (wt %) | | | | | | | | |
|---|---|---|---|---|---|---|---|---|---|
| | Au—S—R | Si—S—R | Al—S—R | Sn—S—R | In—S—R | Fe—S—R | Ga—S—R | Ge—S—R | Ag—S—R |
| 51 | 80~98 | — | 0.5~10 | 0.1~0.5 | 0.1~0.5 | — | — | — | — |
| 52 | 80~98 | — | 0.5~10 | 0.1~0.5 | 0.1~0.5 | 0.1~0.5 | 0.1~0.5 | 0.1~0.5 | — |
| 53 | 80~98 | 0.5~5 | 0.5~5 | 0.1~0.5 | — | — | — | — | 0.5~10 |
| 54 | 80~98 | 0.5~5 | 0.5~5 | — | 0.1~0.5 | — | — | — | 0.5~10 |
| 55 | 80~98 | 0.5~5 | 0.5~5 | — | — | 0.1~0.5 | — | — | 0.5~10 |
| 56 | 80~98 | 0.5~5 | 0.5~5 | — | — | — | 0.1~0.5 | — | 0.5~10 |
| 57 | 80~98 | 0.5~5 | 0.5~5 | — | — | — | — | 0.1~0.5 | 0.5~10 |
| 58 | 79~98 | 0.5~5 | 0.5~5 | 0.1~0.5 | 0.1~0.5 | — | — | — | 0.5~10 |
| 59 | 78~98 | 0.5~5 | 0.5~5 | 0.1~0.5 | 0.1~0.5 | 0.1~0.5 | 0.1~0.5 | 0.1~0.5 | 0.5~10 |
| 60 | 80~98 | 0.5~5 | 0.5~5 | 0.1~0.5 | — | — | — | — | — |
| 61 | 80~98 | 0.5~5 | 0.5~5 | — | 0.1~0.5 | — | — | — | — |
| 62 | 80~98 | 0.5~5 | 0.5~5 | — | — | 0.1~0.5 | — | — | — |
| 63 | 80~98 | 0.5~5 | 0.5~5 | — | — | — | 0.1~0.5 | — | — |
| 64 | 80~98 | 0.5~5 | 0.5~5 | — | — | — | — | 0.1~0.5 | — |
| 65 | 79~98 | 0.5~5 | 0.5~5 | 0.1~0.5 | 0.1~0.5 | — | — | — | — |
| 66 | 78~98 | 0.5~5 | 0.5~5 | 0.1~0.5 | 0.1~0.5 | 0.1~0.5 | 0.1~0.5 | 0.1~0.5 | — |
| 67 | 67~92 | 0.1~3 | — | — | — | — | — | — | — |
| 68 | 67~92 | — | 0.1~3 | — | — | — | — | — | — |
| 69 | 64~92 | 0.1~3 | 0.1~3 | — | — | — | — | — | — |
| 70 | 64~92 | 0.1~3 | 0.1~3 | — | — | — | — | — | — |
| 71 | 65~92 | 0.1~2 | 0.1~2 | 0.1~1 | — | — | — | — | — |
| 72 | 65~92 | 0.1~2 | 0.1~2 | — | 0.1~1 | — | — | — | — |
| 73 | 65~92 | 0.1~2 | 0.1~2 | — | — | 0.1~1 | — | — | — |
| 74 | 65~92 | 0.1~2 | 0.1~2 | — | — | — | 0.1~1 | — | — |
| 75 | 57~92 | 0.1~3 | — | — | — | — | — | — | 0.5~10 |

| Sample No. | Ag fine powder | Kind of eutectic alloy and mixture ratio (wt %) | | | |
|---|---|---|---|---|---|
| | | AuSi | AuAl | AuSn | AuIn |
| 51 | 0.5~10 | — | — | — | — |
| 52 | 0.5~10 | — | — | — | — |
| 53 | — | — | — | — | — |
| 54 | — | — | — | — | — |
| 55 | — | — | — | — | — |
| 56 | — | — | — | — | — |

TABLE 3-continued

| | | | | | |
|---|---|---|---|---|---|
| 57 | — | — | — | — | — |
| 58 | — | — | — | — | — |
| 59 | — | — | — | — | — |
| 60 | 0.5~10 | — | — | — | — |
| 61 | 0.5~10 | — | — | — | — |
| 62 | 0.5~10 | — | — | — | — |
| 63 | 0.5~10 | — | — | — | — |
| 64 | 0.5~10 | — | — | — | — |
| 65 | 0.5~10 | — | — | — | — |
| 66 | 0.5~10 | — | — | — | — |
| 67 | — | 5~30 | — | — | — |
| 68 | — | — | 5~30 | — | — |
| 69 | — | — | — | 5~30 | — |
| 70 | — | — | — | — | 5~30 |
| 71 | — | 5~30 | — | — | — |
| 72 | — | — | 5~30 | — | — |
| 73 | — | — | — | 5~30 | — |
| 74 | — | — | — | — | 5~30 |
| 75 | — | 5~30 | — | — | — |

TABLE 4

| Sample No. | Kind of terpene sulfide compound and mixture ratio (wt %) | | | | | | | | |
|---|---|---|---|---|---|---|---|---|---|
| | Au—S—R | Si—S—R | Al—S—R | Sn—S—R | In—S—R | Fe—S—R | Ga—S—R | Ge—S—R | Ag—S—R |
| 76 | 57~92 | — | 0.1~3 | — | — | — | — | — | 0.5~10 |
| 77 | 57~92 | 0.1~3 | — | — | — | — | — | — | — |
| 78 | 57~92 | — | 0.1~3 | — | — | — | — | — | — |
| 79 | 57~92 | 0.1~3 | — | — | — | — | — | — | — |
| 80 | 57~92 | — | 0.1~3 | — | — | — | — | — | — |
| 81 | 54~92 | 0.1~3 | 0.1~3 | — | — | — | — | — | 0.5~10 |
| 82 | 53~92 | 0.1~3 | 0.1~3 | 0.1~1 | — | — | — | — | 0.5~10 |
| 83 | 53~92 | 0.1~3 | 0.1~3 | — | 0.1~1 | — | — | — | — |
| 84 | 53~92 | 0.1~3 | 0.1~3 | — | — | 0.1~1 | — | — | — |
| 85 | 43~92 | 0.1~3 | 0.1~3 | — | — | — | 0.1~1 | — | — |
| 86 | 57~92 | 0.1~3 | — | — | — | — | — | — | 0.5~10 |
| 87 | 57~92 | — | 0.1~3 | — | — | — | — | — | 0.5~10 |
| 88 | 57~92 | 0.1~3 | — | — | — | — | — | — | — |
| 89 | 70~99 | — | — | — | — | — | — | — | — |
| 90 | 70~99 | — | 0.1~3 | — | — | — | — | — | — |
| 91 | 67~92 | 0.1~3 | — | — | — | — | — | — | — |
| 92 | 67~92 | — | 0.1~3 | — | — | — | — | — | — |
| 93 | 61~92 | 0.1~3 | 0.1~3 | — | — | — | — | — | — |
| 94 | 64~92 | 0.1~1 | 0.1~1 | 0.1~1 | — | — | — | — | — |
| 95 | 64~92 | 0.1~1 | 0.1~1 | — | 0.1~1 | — | — | — | — |
| 96 | 64~92 | 0.1~1 | 0.1~1 | — | — | 0.1~1 | — | — | — |
| 97 | 64~92 | 0.1~1 | 0.1~1 | — | — | — | 0.1~1 | — | — |
| 98 | 57~88 | 0.1~3 | — | — | — | — | — | — | 0.5~10 |
| 99 | 57~88 | — | 0.1~3 | — | — | — | — | — | 0.5~10 |
| 100 | 54~88 | 0.1~3 | — | — | — | — | — | — | — |

| Sample No. | Ag fine powder | Kind of eutectic alloy and mixture ratio (wt %) | | | |
|---|---|---|---|---|---|
| | | AuSi | AuAl | AuSn | AuIn |
| 76 | — | — | 5~30 | — | — |
| 77 | 0.5~10 | — | — | 5~30 | — |
| 78 | 0.5~10 | — | — | — | 5~30 |
| 79 | 0.5~10 | 5~30 | — | — | — |
| 80 | 0.5~10 | — | 5~30 | — | — |
| 81 | — | 5~20 | — | 0.1~10 | — |
| 82 | — | — | 5~20 | 0.1~10 | — |
| 83 | 0.5~10 | 5~20 | — | — | 0.1~10 |
| 84 | 0.5~10 | — | 5~20 | — | 0.1~10 |
| 85 | 0.5~10 | 5~20 | 0.1~10 | — | 0.1~10 |
| 86 | — | 5~20 | — | — | 0.1~10 |
| 87 | — | — | 5~20 | 0.1~10 | — |
| 88 | 0.5~10 | — | — | 5~20 | — |
| 89 | 0.5~10 | 0.1~10 | 0.1~10 | — | — |
| 90 | 0.5~10 | — | — | 0.1~10 | 0.1~10 |
| 91 | — | 5~20 | 1~10 | — | — |
| 92 | — | 5~20 | 1~10 | — | — |
| 93 | — | 5~20 | 1~10 | 0.1~3 | — |
| 94 | — | 5~20 | 1~10 | — | 0.1~3 |
| 95 | — | 5~20 | 1~10 | 0.1~2 | 0.1~1 |

TABLE 4-continued

| | | | | | |
|---|---|---|---|---|---|
| 96 | — | 5~20 | 1~10 | 0.1~1 | 0.1~2 |
| 97 | — | 5~20 | 1~10 | 0.1~2 | 0.1~1 |
| 98 | — | 5~15 | 5~15 | — | — |
| 99 | — | 5~20 | 1~10 | — | — |
| 100 | 0.5~10 | 5~15 | 5~15 | 0.1~3 | — |

TABLE 5

| Sample No. | Kind of terpene sulfide compound and mixture ratio (wt %) | | | | | | | |
|---|---|---|---|---|---|---|---|---|
| | Au—S—R | Si—S—R | Al—S—R | Sn—S—R | In—S—R | Fe—S—R | Ga—S—R | Ge—S—R | Ag—S—R |
| 101 | 51~88 | — | 0.1~3 | — | — | — | — | — | — |
| 102 | — | — | — | — | — | — | — | — | — |

| Sample No. | Ag fine powder | Kind of eutectic alloy and mixture ratio (wt %) | | | |
|---|---|---|---|---|---|
| | | AuSi | AuAl | AuSn | AuIn |
| 101 | 0.5~10 | 5~15 | 5~15 | — | 0.1~3 |
| 102 | — | — | — | — | — |

TABLE 6

| Sample No. | Kind of terpene sulfide compound and mixture ratio (wt %) | | | | | | | |
|---|---|---|---|---|---|---|---|---|
| | Au—S—R | Si—S—R | Al—S—R | Sn—S—R | In—S—R | Fe—S—R | Ga—S—R | Ge—S—R | Ag—S—R |
| 103 | 67~92 | 0.1~3 | — | — | — | — | — | — | — |
| 104 | 67~92 | — | 0.1~3 | — | — | — | — | — | — |
| 105 | 64~92 | 0.1~3 | 0.1~3 | — | — | — | — | — | — |
| 106 | 64~92 | 0.1~3 | 0.1~3 | — | — | — | — | — | — |
| 107 | 65~92 | 0.1~2 | 0.1~2 | 0.1~1 | — | — | — | — | — |
| 108 | 65~92 | 0.1~2 | 0.1~2 | — | 0.1~1 | — | — | — | — |
| 109 | 65~92 | 0.1~2 | 0.1~2 | — | — | 0.1~1 | — | — | — |
| 110 | 65~92 | 0.1~2 | — | — | — | — | 0.1~1 | — | — |
| 111 | 57~92 | 0.1~3 | — | — | — | — | — | — | 0.5~10 |
| 112 | 57~92 | — | 0.1~3 | — | — | — | — | — | 0.5~10 |
| 113 | 57~92 | 0.1~3 | — | — | — | — | — | — | — |
| 114 | 57~92 | — | 0.1~3 | — | — | — | — | — | — |

| Sample No. | Ag fine powder | Kind of eutectic alloy and mixture ratio (wt %) | | | |
|---|---|---|---|---|---|
| | | AuSi | AuAl | AuSn | AuIn |
| 103 | — | 5~30 | — | — | — |
| 104 | — | — | 5~30 | — | — |
| 105 | — | — | — | 5~30 | — |
| 106 | — | — | — | — | 5~30 |
| 107 | — | 5~30 | — | — | — |
| 108 | — | — | 5~30 | — | — |
| 109 | — | — | — | 5~30 | — |
| 110 | — | — | — | — | 5~30 |
| 111 | — | 5~30 | — | — | — |
| 112 | — | — | 5~30 | — | — |
| 113 | 0.5~10 | — | — | 5~30 | — |
| 114 | 0.5~10 | — | — | — | 5~30 |

In Tables 1 to 6, {Au—S—R} indicates gold terpene sulfide, which is a compound of Au, S and $(C_5H_8)_n$, i.e., {Au—S—$(C_5H_8)_n$}. For example, $(C_5H_8)_n$, is hemiterpene with n=1, monoterpene with n=2, sesquiterpene with n=3, diterpene with n=4, sesterterpene with n=5, triterpene with n=6, tetraterpene with n=8, or polyterpene with n≧9, which shall be apply hereinafter.

The gold terpene sulfide is produced as follows, for example.

(1) Gold is dissolved in aqua regia to produce a solution of $HAuCl_4 \cdot 4H_2O$ (gold chloride), which is dissolved in the same amount of ethyl alcohol.

(2) Sulfur powder is added to a turpentine oil to produce a balsam sulfide solution being as a saturated solution.

(3) The solution finally obtained in the step (1) is added to the balsam sulfide solution obtained in the step (2) and heat-reacted on the water bath at 60° C.–75° C. to obtain precipitate of powder (the size of particle is 0.1 μm–10 μm) of gold terpene sulfide {Au—S—$C_{10}H_{16}$}.

(4) In order to separate the gold terpene sulfide obtained in the step (3) and resin component of reaction residue, ethyl alcohol is added to dissolve the resin component and the powder of gold terpene sulfide is re-precipitated.

(5) After the precipitate of gold terpene sulfide and the resin ester obtained in the step (4) are sufficiently separated, only the resin ester solution is discarded. Then the precipitate is dried to obtain powder of gold terpene sulfide, or the precipitate of resinate of gold and the resin ester solution are sufficiently stirred and then separated with a filter paper and dried.

In Tables 1 to 6, {Si—S—R} indicates silicon terpene sulfide, which is a compound of Si, S and $(C_5H_8)_n$, {Si—S—$(C_5H_8)_n$}. It is obtained in the manufacturing process given below, for example.

(1) Silicon is dissolved in a solution of about 5–10% hydrofluoric acid in aqua regia to produce a solution of silicon tetrafluoride ($SiF_4$), which is dissolved in the same amount of ethyl alcohol.

(2) Powder of sulfur is added to a turpentine oil to produce a balsam sulfide solution being as a saturated solution.

(3) The solution finally obtained in the step (1) is added to the balsam sulfide solution obtained in the step (2), which is heating-reacted on the water bath at 60° C.–75° C. to produce a solution of resinate of silicon. (4) NaOH is added to the resinate solution of silicon obtained in the step (3) and sufficiently stirred until the solution PH indicates neutral.

(5) In order to separate the resin component which is reaction residue from the solution obtained in the step (4), ethyl alcohol is added to dissolve the resin component and powder of resinate of silicon containing silicon terpene sulfide (the size of particle is 0.1 μm–10 μm) is precipitated, which is separated with a filter paper and dried.

In Tables 1 to 6, {Al—S—R} indicates aluminum terpene sulfide, which is a compound of Al, S and $(C_5H_8)_n$, {Al—S—$(C_5H_8)_n$}. It is obtained in the manufacturing process given below, for example.

That is to say, aluminum is dissolved in aqua regia to produce a solution of aluminum terpene chloride, which is dissolved in the same amount of ethyl alcohol. Then the same steps as the manufacturing steps (2) to (5) for silicon terpene sulfide described above are conducted and then fine powder (particle size of 0.1 μm–10 μm) of resinate of aluminum terpene sulfide containing aluminum terpene sulfide is obtained.

In Tables, {Sn—S—R} indicates tin terpene sulfide, which is a compound of Sn, S and $(C_5H_8)_n$, i.e., {Sn—S—$((C_5H_8)_n$}. The (In—S—R} indicates indium terpene sulfide, which is a compound of In, S and $(C_5H_8)_n$, {In—S—$(C_5H_8)_n$}. The {Fe—S—R} indicates iron terpene sulfide, which is a compound of Fe, S and $(C_5H_8)_n$, {Fe—S—$(C_5H_8)_n$}. The {Ga—S—R} indicates gallium terpene sulfide, which is a compound of Ga, S and $(C_5H_8)_n$, {Ga—S—$(C_5H_8)_n$}. The {Ge—S—R} indicates germanium terpene sulfide, which is a compound of Ge, S and $(C_5H_8)_n$, {Ge—S—$(C_5H_8)_n$}. The {Ag—S—R} indicates silver terpene sulfide, which is a compound of Ag, S and $(C_5H_8)_n$, {Ag—S—$(C_5H_8)_n$}. These terpene sulfide compounds are produced in process similar to the above-described process for aluminum terpene sulfide. In the columns "Kind of binary eutectic alloy and mixture ratio (weight percentage)" in Tables 3 to 5, AuSi indicates a binary eutectic alloy of gold and silicon, AuAl indicates a binary eutectic alloy of gold and aluminum, AuSn indicates a binary eutectic alloy of gold and tin, and AuIn indicates a binary eutectic alloy of gold and indium. In the columns of "Kind of alloy and mixture ratio (weight percentage)" in Table 6, AuSiAl indicates an alloy of gold, silicon and aluminum, AuAlSn indicates an alloy of gold, aluminum and tin, AuSnIn indicates an alloy of gold, tin and indium, and AuInSiAlSn indicates an alloy of gold, indium, silicon, aluminum and tin.

In Table 1, the sample No. 1 indicates a surface treatment material 2 required in fusing dental porcelain in which the mixture ratio of gold terpene sulfide powder:silicon terpene sulfide powder is set to 87–99:1–13% by weight, the sample No. 2 indicates a surface treatment material 2 required in fusing dental porcelain in which the mixture ratio of gold terpene sulfide powder:aluminum terpene sulfide powder is set to 87–99:1–13% by weight, and the sample No. 3 indicates a surface treatment material 2 required in fusing dental porcelain in which the mixture ratio of gold terpene sulfide powder:silicon terpene sulfide powder:aluminum terpene sulfide powder is set to 87–99:0.5–6.5:0.5–6.5% by weight.

Similarly, the sample No. 4 and so on shown in Tables 1 to 6 show surface treatment materials 2 required in fusing dental porcelain which are mixture of the powders in the ratio (weight percentage) indicated in the component columns.

In Tables 1 to 6, while it is clear that the samples of all sample numbers are included in claim 1 of the present invention, the samples No. 1 to No. 3 are shown particularly to describe an embodiment of the surface treatment material required in fusing dental porcelain of claim 2 of the present invention, the samples No. 4 to No. 20 are shown particularly to describe an embodiment of the surface treatment material required in fusing dental porcelain of claim 3 of the present invention, and the samples No. 21 to No. 66 are shown particularly to describe an embodiment of the surface treatment material required in fusing dental porcelain of claim 4 of the present invention.

It is also possible to use, as a surface treatment material required in fusing dental porcelain, one selected from the samples No. 1 to No. 66 further containing one or more kinds of powders out of powder of binary eutectic alloy of gold and silicon, powder of binary eutectic alloy of gold and aluminum, powder of binary eutectic alloy of gold and tin, and powder of binary eutectic alloy of gold and indium, which corresponds to claim 5 of the present invention. The surface treatment materials included in claim 5 of this invention are shown in Tables 3 to 5 as samples No. 67 to No. 102.

Furthermore, it is also possible to use, as a surface treatment material required in fusing dental porcelain, one sample selected from the samples No. 1 to No. 66 further containing powder obtained by alloying a combination of two or more selected from silicon, aluminum, tin and indium with gold, which corresponds to claim 6 of this invention. The surface treatment materials required in fusing dental porcelain included in claim 6 of the invention are shown in Table 6 as samples No. 103 to No. 114.

Production of the powder of binary eutectic alloy of gold and silicon, the powder of binary eutectic alloy of gold and aluminum, the powder of binary eutectic alloy of gold of tin, and the powder of binary eutectic alloy (it may be Hypo-eutectic alloy or Hyper-eutectic alloy) of gold and indium, and production of the alloyed powder of a combination of two or more kinds selected from silicon, aluminum, tin and indium with gold are 15 conducted as follows. That is to say, the eutectic alloy or alloy is heated to melt and the solidus metal is dropped into water little by little for preprocessing, and then roughly ground (random particles of about a diameter of 5–20 mm), which is primary ground for about 6 to 8 hours in a stamp mill to particle size of about 10–50 μm. Next, it is finish ground for about 2 to 3 hours in a planetary pot mill to obtain alloy particles adjusted to particle size of 0.2–10 μm.

Next, the process of fusing a dental porcelain on a metal frame 1 using the surface treatment material required in fusing dental porcelain according to the embodiments above will be described.

Figure 4:
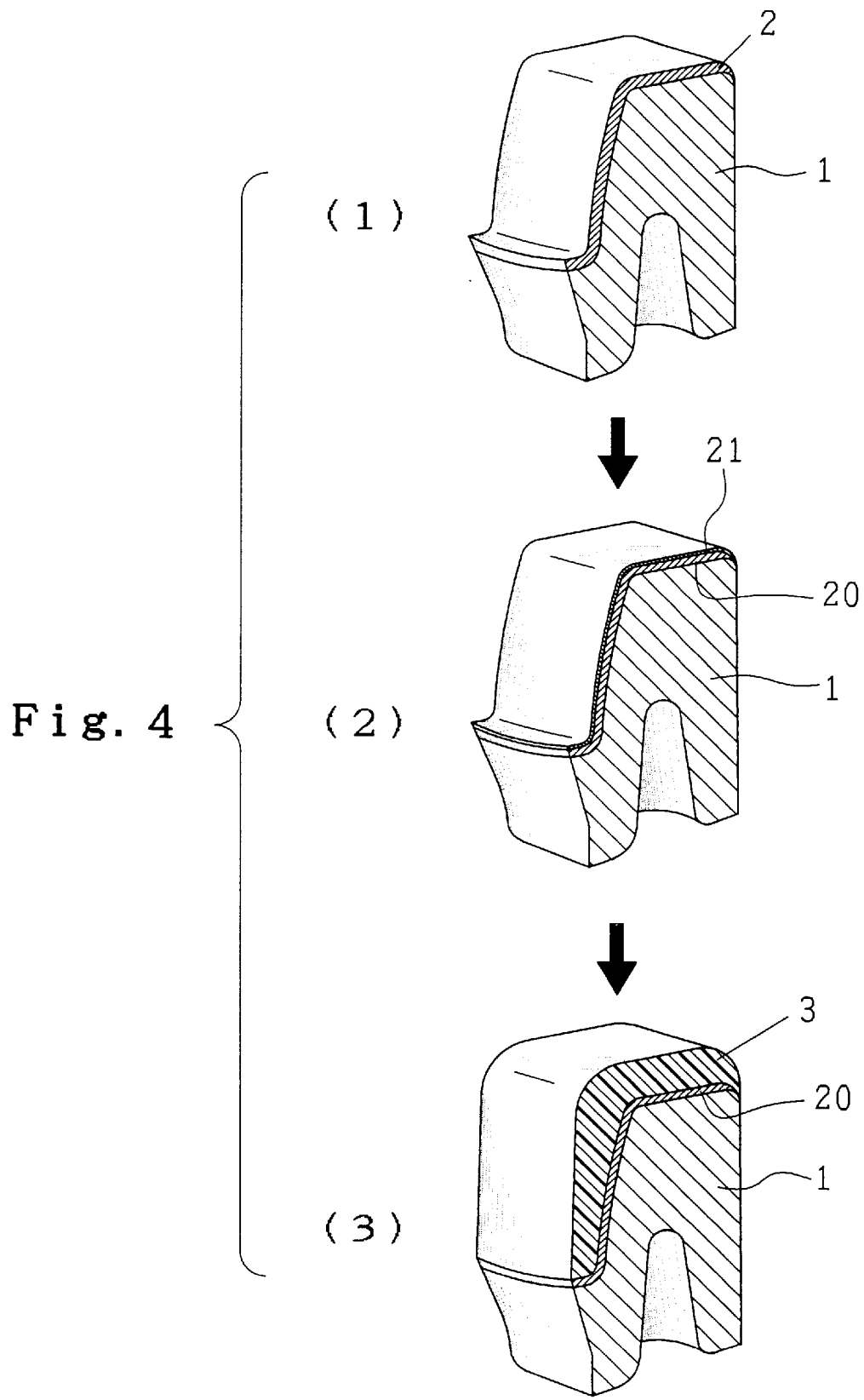
FIG. 4 is a diagram showing process of fusing a dental porcelain on a metal frame using a conventional surface treatment material required in fusing dental porcelain.

The surface treatment material required in fusing dental porcelain of the sample No. 1 above kneaded with a binder into paste was applied on a metal frame 1 in the procedure described in the conventional example above and sintered for one to two minutes at 900° C.–960° C. Then as shown in FIG. 1(1), only an alloy layer of gold and silicon was formed as a surface treatment layer 20 on the surface of the metal frame 1, but nothing like the coat 21 shown in FIG. 4(2) was formed on the surface. This is considered that sulfur in gold terpene sulfide and silicon terpene sulfide volatilized as $SO_2$ and terpene $(C_5H_8)_n$, were decomposed into $CO_2$ and $H_2O$ and released into the air, with gold and silicon remaining alone. The surface treatment material required in fusing dental porcelain of the sample No. 2, kneaded with binder into paste, was sintered on the surface of the metal frame 1 under the same temperature condition for the same time as described above, then an alloy layer of gold and aluminum was formed on the surface of the metal frame 1 as a surface treatment layer. In the case of the samples No. 3 and so on, sulfur and terpene similarly disappeared and an alloy layer (surface treatment layer) of other metals was formed on the surface of the metal frame 1.

When the surface treatment materials required in fusing dental porcelain of the sample Nos. 23, 24, 32–38, 46–52, 60–114 were sintered on the surface of the metal frame 1, they could also be sintered on the metal frame 1 without requiring use of a special antioxidant. This is considered that terpene and sulfur contained in gold terpene sulfide and the like exhibit the oxidation suppressing function as described about the surface treatment material required in fusing dental porcelain of the sample No. 1, and further, the oxidation suppressing function is exhibited significantly because the ratios of the components, are large, and then oxidation of each binary eutectic alloy or the like is prevented.

Accordingly, unlike the conventional one, the samples above can be sintered to the metal frame 1 without use of a particular antioxidant, so that a coat of an antioxidant is not deposited, as in the case of the conventional one, on the surface of the surface treatment layer 20 formed on the metal frame 1 after sintering the surface treatment material 2 required in fusing dental porcelain. This eliminates the need of cleaning process after sintering.

After that, with a dental porcelain put on the surface of the surface treatment layer 20 formed on the surface of the metal 20 frame 1, it is fused for four to eight minutes at 700°C.–960° C. Then the gold component or the like contained in the surface treatment layer 20 penetrates into the texture of the other to form diffusion solid solution with alloy component of the metal frame 1. Components of silicon, aluminum, tin, indium and iron contained in each terpene sulfide compound or each binary eutectic alloy and other alloys or the like form diffusion solid solution with the dental porcelain component and thereby the dental porcelain is bonded and fixed to the metal frame 1. Furthermore, as is well known, germanium and gallium contained in the terpene sulfide compound or each binary eutectic alloy and other alloys or the like have the effect of allowing a decrease of sintering temperature for each surface treatment material required in fusing dental porcelain to the metal frame 1.

An experiment conducted by the inventor confirmed that any of the above surface treatment materials 2 required in fusing dental porcelain sufficiently exhibited generally required bonding strength.

That is to say, it was confirmed that the samples No. 1–No. 3 presented a bonding strength of 20–50 MPa, the samples No. 4–No. 20 presented a bonding strength of 18–53 MPa, the samples No. 21–No. 66 presented a bonding strength of 24–83 MPa, and the samples No. 67 and so on presented a bonding strength of 25–72 MPa, respectively. It was also confirmed that the known Blendgold Spezial (gold alloy) as a trademark (produced by Heraeus in Germany) presented a bonding strength of 13–17 MPa, the Blendgold Neu (gold alloy) as a trademark (produced by Heraeus in Germany) presented a bonding strength of 25–55 MPa, and directly fusing the dental porcelain on the metal frame 1 without using a surface treatment material required in fusing dental porcelain presented a bonding strength of 12–25 MPa.

The bonding strengths above are values (MPa) which were measured when the test piece of FIG. 2 was tested by a punching shearing test, which were obtained by the expression given below.

$$MPa=W/(0.102\pi dL)$$

Figure 2:
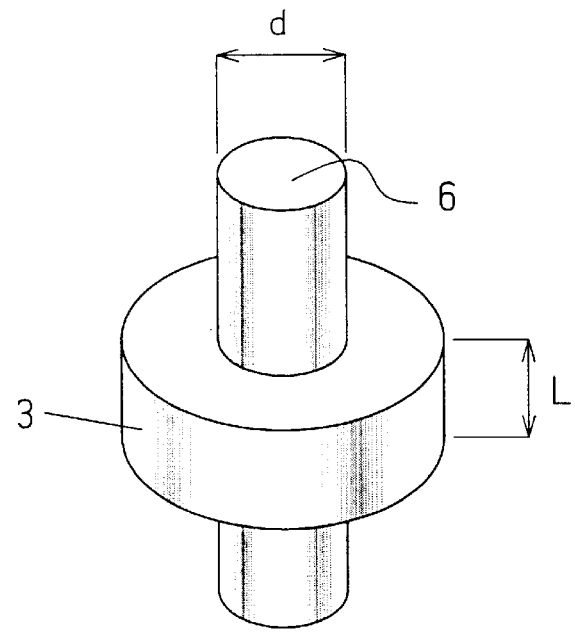
FIG. 2 is a perspective view of the appearance of a test piece used in punching shearing test in the embodiment of the present invention.

In the expression above, d and L are dimensions of each part of the test piece shown in FIG. 2 (unit:mm), π is the ratio of the circumference to its diameter, and W is a load (unit:kgf) when sheared.

Figure 3:
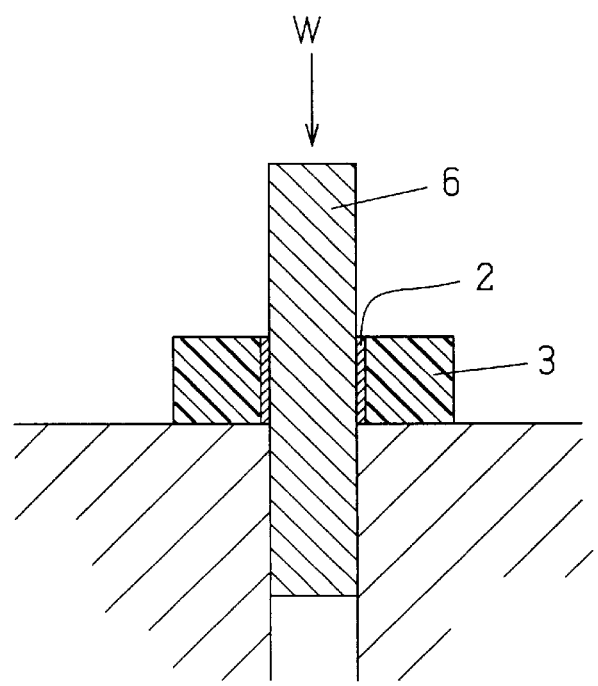
FIG. 3 is a sectional view of the test piece used in the punching shearing test in the embodiment of the present invention.

The section of this test piece has the structure shown in FIG. 3, which was obtained by firing (at the same sintering temperature and for the same sintering time as those in sintering on the metal frame described before) a surface treatment material 2 required in fusing dental porcelain of each sample number in the same area as the porcelain formation area of a shaft 6 formed of a metal frame material of the company to which the inventor belongs (Trade name: Blendy N-78, Composition: 78 weight % gold, 9.3 weight % platinum, 8.7 weight % palladium, 1.5 weight silver, 1.0 weight % indium, and others 1.5 weight %), and building up in a ring and fusing (at the same fusing temperature and for the same fusing time as those for fusing the dental porcelain already described) the dental porcelain 3 on this surface treatment material 2 required in fusing dental porcelain The dental porcelain 3 used in the shearing test was trade name: Noritake, Super Porcelain AAA produced by Noritake.

While sulfur powder is added to a turpentine oil in the process of producing terpene sulfide compounds in the embodiments described above, a lavender oil, a camphor oil, rosemary oil, an eucalyptus oil, a safrole oil and the like can be used instead of the turpentine oil.

While the invention has been described in detail, the foregoing description is in all aspects illustrative and, not restrictive. It is understood that numerous other modifications and variations can be devised without departing from the scope of the invention.

I claim:

1. A surface treatment material used for fusing a dental porcelain on a metal frame, comprising:

a powder of gold terpene sulfide; and at least one of a powder of silicon terpene sulfide and a powder of aluminum terpene sulfide.

2. A surface treatment material used for fusing a dental porcelain on a metal frame, comprising:

a powder of gold terpene sulfide; and at least one of a powder of tin terpene sulfide, a powder of indium terpene sulfide and a powder of iron terpene sulfide.

3. A surface treatment material used for fusing a dental porcelain on a metal frame, comprising:

a powder of gold terpene sulfide; and at least one of a powder of a binary eutectic alloy of gold and silicon, a powder of a binary eutectic alloy of gold and aluminum, a powder of a binary eutectic alloy of gold and tin, and a powder of a binary eutectic alloy of gold and indium.

4. A surface treatment material used for fusing a dental porcelain on a metal frame, comprising:

a powder of gold terpene sulfide; and an alloyed powder comprised of at least two of silicon, aluminum, tin, and indium with gold.

5. The surface treatment material according to claim 2, further comprising one of a powder of silver terpene sulfide, and a powder of silver.

6. The surface treatment material according to claim 2, further comprising at least one of a powder of a binary eutectic alloy of gold and silicon, a powder of a binary eutectic alloy of gold and aluminum, a powder of a binary eutectic alloy of gold and tin, and a power of a binary eutectic alloy of gold and indium.

7. A surface treatment material used for fusing a dental porcelain on a metal frame, comprising:

a powder of gold terpene sulfide;

one of a powder of silver terpene sulfide and a powder of silver; and at least one of a powder of a binary eutectic alloy of gold and silicon, a powder of a binary eutectic alloy of gold and aluminum, a powder of a binary eutectic alloy of gold and tin, and a powder of a binary eutectic alloy of gold and indium.

8. The surface treatment material according to claim 2, further comprising an alloyed powder comprised of at least two of silicon, aluminum, tin, and indium with gold.

9. A surface treatment material used for fusing a dental porcelain on a metal frame, comprising:

a powder of gold terpene sulfide;

one of a powder of silver terpene sulfide and a powder of silver; and an alloyed powder comprised of at least two of silicon, aluminum, tin, and indium with gold.

10. The surface treatment material according to 1, further comprising at least one of a powder of tin terpene sulfide, a powder of indium terpene sulfide and a powder of iron terpene sulfide.

11. The surface treatment material according to 1, further comprising one of a powder of silver terpene sulfide, and a powder of silver.

12. The surface treatment material according to claim 1, further comprising at least one of a powder of a binary eutectic allow of gold and silicon, a powder of a binary eutectic alloy of gold and aluminum, a powder of a binary eutectic alloy of gold and tin, and a powder of a binary eutectic alloy of gold and indium.

13. The surface treatment material according to claim 1, further comprising an alloyed powder comprised of at least two of silicon, aluminum, tin, and indium with gold.

* * * * *